(12) United States Patent
Manhart (10) Patent No.: US 12,039,703 B2
(45) Date of Patent: Jul. 16, 2024

(54) PROVISION OF AN OPTIMUM SUBTRACTION DATA SET

(71) Applicant: Siemens Healthcare GmbH, Erlangen (DE)

(72) Inventor: Michael Manhart, Fürth (DE)

(73) Assignee: SIEMENS HEALTHINEERS AG, Erlangen (DE)

( * ) Notice: Subject to any disclaimer, the term of this patent is extended or adjusted under 35 U.S.C. 154(b) by 324 days.

(21) Appl. No.: 17/523,889

(22) Filed: Nov. 10, 2021

(65) Prior Publication Data

US 2022/0156905 A1   May 19, 2022

(30) Foreign Application Priority Data

Nov. 13, 2020   (DE) .................. 10 2020 214 323.4

(51) Int. Cl.
*G06T 5/50*  (2006.01)
*G06T 7/00*  (2017.01)
*G16H 30/40*  (2018.01)

(52) U.S. Cl.
CPC .............. *G06T 5/50* (2013.01); *G06T 7/0016* (2013.01); *G16H 30/40* (2018.01); *G06T 2207/10081* (2013.01); *G06T 2207/10088* (2013.01); *G06T 2207/10104* (2013.01); *G06T 2207/10116* (2013.01); *G06T 2207/10132* (2013.01);
(Continued)

(58) Field of Classification Search
CPC ..................... G06T 5/50; G06T 7/0016; G06T 2207/10081; G06T 2207/10088; G06T 2207/10104; G06T 2207/10116; G06T 2207/10132; G06T 2207/20216; G06T 2207/20224; G06T 2207/30168;
(Continued)

(56) References Cited

U.S. PATENT DOCUMENTS

2007/0195932 A1   8/2007   Nakaura et al.
2014/0016844 A1   1/2014   Afanasenko
(Continued)

FOREIGN PATENT DOCUMENTS

DE   102019202514 A1   8/2020
JP   2007195633 A   8/2007

OTHER PUBLICATIONS

German Office Action for German Application No. 10 2020 214 323.4 dated Sep. 16, 2021.

*Primary Examiner* — Stephen P Coleman
(74) *Attorney, Agent, or Firm* — Lempia Summerfield Katz LLC (57) ABSTRACT

A method for providing an optimum subtraction data set includes receiving first image data sets that are recorded by a medical imaging device and map an examination object within a first temporal phase. At least one second image data set that maps the examination object within a second temporal phase and is recorded by the same or another medical imaging device is received. Mask data sets are determined. The mask data sets include at least one of the first image data sets and/or an averaging of at least one combination of the first image data sets. Subtraction data sets are generated by subtracting one of the mask data sets from the at least one second image data set, and an image quality parameter is determined for each of the subtraction data sets. An optimum subtraction data set is provided by a comparison of the image quality parameters.

18 Claims, 4 Drawing Sheets

(52) U.S. Cl.
CPC ............... *G06T 2207/20216* (2013.01); *G06T 2207/20224* (2013.01); *G06T 2207/30168* (2013.01)

(58) Field of Classification Search
CPC .......... G06T 2207/30101; G16H 30/40; A61B 6/4441; A61B 6/481; A61B 6/504; A61B 6/5205
USPC ........................................................ 382/130
See application file for complete search history.

(56) References Cited

U.S. PATENT DOCUMENTS

| | | |
|---|---|---|
| 2018/0279983 A1 | 10/2018 | Ohishi |
| 2020/0226405 A1* | 7/2020 | Huber, Jr. ............... G06F 18/24 |
| 2020/0273217 A1 | 8/2020 | Kaethner et al. |

* cited by examiner

PROVISION OF AN OPTIMUM SUBTRACTION DATA SET

This application claims the benefit of German Patent Application Number DE 10 2020 214 323.4, filed on Nov. 13, 2020, which is hereby incorporated by reference in its entirety.

BACKGROUND

The present embodiments relate to a method for providing an optimum subtraction data set, a medical imaging device, and a computer program product.

To record changes over time in an examination area of an examination object (e.g., a human and/or animal patient), X-ray-based imaging methods are often used (e.g., in the context of dynamic perfusion imaging). The change over time to be detected may include, for example, a propagation movement and/or flow movement of a contrast medium (e.g., a contrast medium flow and/or a contrast medium bolus) in a hollow organ (e.g., a vessel section) of the examination object.

The X-ray-based imaging methods often include digital subtraction angiography (DSA), where at least two X-ray images recorded in chronological order, which at least partially map the common examination area, are subtracted from one another. In the case of a DSA, a distinction is also often made between a mask phase for recording at least one mask image and a filling phase for recording at least one filling image. The mask image may often map the examination area without a contrast medium. Further, the filling image may map the examination area while the contrast medium is arranged therein. As a result of DSA, a difference image is often provided by subtracting the mask and filling image. As a result, the components in the difference image that are irrelevant and/or interfere with treatment and/or diagnosis, which are, for example, unchanging over time, may often be reduced and/or removed.

Movements of the examination object (e.g., between the mask and filling phase) may disadvantageously result in motion artifacts in the difference image.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved image quality in the mapping of changes in an examination object is provided.

In a first aspect, the present embodiments relate to a method for providing an optimum subtraction data set. In a first act a), first image data sets are received. The first image data sets map an examination object within a first temporal phase. Further, the first image data sets are recorded by a medical imaging device. In a second act b), at least one second image data set is received. The at least one second image data set maps the examination object within a second temporal phase. Further, the at least one second image data set is recorded by the medical imaging device or another medical imaging device. In addition, the at least one second image data set maps a change in the examination object compared to the first temporal phase. In a third act c), mask data sets are determined. The mask data sets include at least one of the first image data sets and/or an averaging of at least one combination of the first image data sets. In a fourth act d), subtraction data sets are generated in each case by subtracting one of the mask data sets from the at least one second image data set. Further, in a fifth act e), an image quality parameter is determined for each of the subtraction data sets. In a sixth act f), an optimum subtraction data set is provided by comparing the image quality parameters.

Receiving the first image data sets and/or the at least one second image data set may, for example, include capturing and/or reading out a computer-readable data memory and/or receiving from a data storage unit (e.g., a database). Further, the first image data sets may be provided by a provision unit of the medical imaging device. In addition, the at least one second image data set may be provided by a provision unit of the same and/or a further medical imaging device.

The examination object may, for example, be a human and/or animal patient. Further, the examination object may have an examination area. The examination area may, for example, include a spatial section (e.g., a volume) of the examination object, which has a hollow organ. The hollow organ may, for example, include a lung and/or a vessel segment (e.g., an artery, and/or vein, and/or a heart).

The first image data sets may include a two-dimensional (2D) and/or three-dimensional (3D) image of the examination object (e.g., of the examination area). Further, the first image data sets may map the examination object in a time-resolved manner. For example, the first image data sets may map the examination object at different points in time in each case. The first image data sets may also each be reconstructed from a plurality of first individual images, each of which has an image of at least one section of the examination object. Further, the first image data sets may have metadata. The metadata may include, for example, information relating to a recording parameter and/or operating parameters of the medical imaging device.

The first image data sets may map the examination object within a first temporal phase (e.g., a mask phase). For this purpose, the first image data sets may be recorded within a predefined first period.

The at least one second image data set may include a two-dimensional (2D) and/or three-dimensional (3D) image of the examination object (e.g., of the examination area). Further, the at least one second image data set may map the examination object in a time-resolved manner. The at least one second image data set may also, in each case, be reconstructed from a plurality of second individual images, each of which has an image of at least one section of the examination object. Further, the at least one second image data set may have metadata. The metadata may include, for example, information relating to a recording parameter and/or operating parameters of the medical imaging device.

The at least one second image data set may map the examination object within a second temporal phase (e.g., a filling phase). For this purpose, the at least one second image data set may be recorded within a predefined second period. In one embodiment, the second temporal phase may be downstream of the first temporal phase.

Further, the at least one second image data set may map a change in the examination object compared to the first temporal phase. The change in the examination object may be, for example, a contrast medium (e.g., a contrast medium flow) and/or a medical object (e.g., a diagnostic and/or surgical instrument) that is at least partially arranged in the examination object during the second temporal phase. For example, the change in the examination object may include a temporal and/or spatial change.

The first image data sets and/or the at least one second image data set may each have a plurality of pixels (e.g., pixels and/or voxels). If the first image data sets and/or the at least one second image data set are time-resolved, the pixels may each have a time intensity curve.

In act c), a plurality of mask data sets (e.g., at least partially different mask data sets) may be determined. The mask data sets may include at least one (e.g., a plurality or all) of the first image data sets. This may make it possible that the mask data set for generating the optimum subtraction data set may have been determined from one of the first image data sets. With regard to the positioning of the examination object, this first image data set may have the greatest possible correspondence with the at least one second image data set and/or minimal noise and/or minimal image artifacts.

Alternatively or additionally, the mask data sets may include averaging (e.g., weighted averaging) of at least one combination (e.g., a plurality of combinations) of the first image data sets. For this purpose, at least two of the first image data sets may be averaged. In this case, the averaging of the at least one combination of first image data sets may take place (e.g., in pixels and/or regionally and/or in a weighted manner). By averaging the at least one combination of the first image data sets, image artifacts (e.g., motion artifacts and/or metal artifacts) and/or noise may be reduced (e.g., quantitatively).

The mask data sets determined in act c) may match the first image data sets and/or the at least one second image data set in terms of their spatial dimensionality and/or resolution. Alternatively or additionally, the determination of the mask data sets may include an interpolation and/or a binning of pixels of the first image data sets.

In act d), a plurality of subtraction data sets may be generated by subtracting one of the mask data sets from the at least one second image data set (e.g., in pixels). For example, to generate the subtraction data sets, each of the mask data sets may be subtracted from the at least one second image data set. If a plurality of second image data sets are received in act b), each of the mask data sets may be subtracted from each of the second image data sets to generate the subtraction data sets. The subtraction data sets may each map the differences (e.g., the change) between the first temporal phase and the second temporal phase on the examination object. Further, the subtraction data sets may have image artifacts. The image artifacts may be caused by a movement of the examination object between the recording of the first image data sets and/or the at least one second image data set. The subtraction data sets may each have a two-dimensional (2D) and/or three-dimensional (3D) image of the change. In addition, the subtraction data sets may be time-resolved.

In act e), in each case, an image quality parameter may be determined for the subtraction data sets (e.g., for each of the subtraction data sets). The image quality parameters may evaluate an artifact level (e.g., an expression of image artifacts) and/or a signal-to-noise-ratio (SNR) in the respective subtraction data set. The image quality parameters may consequently have a value (e.g., a normalized value) that evaluates the image quality of the respective subtraction data set.

Hereinafter, the image quality parameter of the subtraction data sets may be compared in act f). In one embodiment, by comparing the image quality parameters, the subtraction data set may be identified from the plurality of subtraction data sets that have an image quality parameter that is optimum in terms of image quality. The identified subtraction data set may then be provided as the optimum subtraction data set.

By comparing the image quality parameters to identify the optimum subtraction data set from the plurality of subtraction data sets, the subtraction data sets that have image artifacts (e.g., motion artifacts and/or metal artifacts) and/or noise may be excluded. The optimum subtraction data set may consequently have been generated by subtracting the mask data set from the at least one second image data set. The mask data set has the greatest possible correspondence with the at least one second image data set and/or minimal noise and/or minimal image artifacts with regard to the positioning of the examination object.

The mask data set for generating the optimum subtraction data set may have been determined in act c) from a combination of at least two of the first image data sets. These at least two first image data sets may have the greatest possible correspondence with one another and/or with the at least one second image data set with regard to the positioning of the examination object. In addition, these at least two first image data sets may each have minimal noise and/or minimal image artifacts.

Further, the provision of the optimum subtraction data set in act f) may include, for example, storage on a computer-readable storage medium and/or display on a display unit and/or transfer to a provision unit. For example, a graphical representation of the optimum subtraction data set may be displayed on the display unit.

The embodiment enables the image quality of subtraction data sets to be improved by comparing the image quality parameters for the subtraction data sets that have been generated from different combinations of first image data sets and the at least one second image data set. In the case of a movement of the examination object during and/or between the recording of the first image data sets and/or the at least one second image data set, motion artifacts in the subtraction data set may be minimized by the method. For example, improved perfusion imaging may be made possible by the method of one or more of the present embodiments. Perfusion maps may be calculated from the optimum subtraction data set.

In a further embodiment of the method, the mask data sets may include averaging of all possible combinations of the first image data sets.

The possible combinations of the first image data sets may include, for example, all combinations of two or more different first image data sets. If the determination of the mask data sets in act c) includes a weighted averaging of the combinations of the first image data sets, the possible combinations of the first image data sets may also include different permutations of the first image data sets.

The embodiment may provide that none of the possible combinations of the first image data sets for determining the subtraction data sets and thus for determining the optimum subtraction data set is overlooked. In one embodiment, the optimum subtraction data set, which may be determined from the first image data sets and the at least one second image data set, may thereby be provided in act f).

In a further embodiment of the method, the first image data sets may have a plurality of first projection images of the examination object along at least one first projection direction. In addition, the at least one second image data set may have at least one second projection image of the examination object along at least one second projection direction. At least one of the first projection directions and at least one of the second projection directions may correspond.

The medical imaging device for recording the plurality of first projection images and/or the at least one second projection image may have a source and a detector that may be positioned in a defined arrangement. In one embodiment of the medical imaging device as a medical X-ray device (e.g., as a medical C-arm X-ray device) and/or computed tomography system, the source may be an X-ray source, and the detector may be an X-ray detector.

The at least one first projection direction may describe a course of a beam (e.g., a central and/or center beam) between the source and the detector (e.g., a detector center point) of the medical imaging device at the time of recording the respective first projection image. For example, the at least one first projection direction may describe an angulation of the medical imaging device with respect to the examination object and/or an isocenter.

Analogously thereto, the at least one second projection direction may describe a course of a beam between the source and the detector of the medical imaging device and/or of the further medical imaging device at the time of recording the respective second projection image. For example, the at least one second projection direction may describe an angulation of the medical imaging device and/or of the further medical imaging device with respect to the examination object and/or a further isocenter.

The isocenter may describe a spatial point around which the defined arrangement of source and detector may be moved (e.g., rotated) during, for example, the recording of the first projection images. In one embodiment, the at least one first projection direction (e.g., all the first projection directions) may run through the isocenter.

Analogously thereto, the further isocenter may describe a spatial point around which the defined arrangement of source and detector may be moved (e.g., rotated) during, for example, the recording of the second projection images. In one embodiment, the at least one second projection direction (e.g., all the second projection directions) may run through the further isocenter. In one embodiment, the isocenter and the further isocenter may correspond.

In one embodiment, at least one of the first projection directions may coincide with at least one of the second projection directions. As a result, a corresponding imaging geometry between at least some of the first projection images and the at least one second projection image may be provided.

In a further embodiment of the method, the first image data sets and the at least one second image data set may each map at least one common slice and/or an at least partially common volume of the examination object. In one embodiment, at least one of the mask data sets includes an averaging of at least one combination of the first image data sets. Further, in act c), to determine the mask data sets, the at least one combination of the first image data sets may be averaged in layers and/or in lines and/or in columns and/or in pixels. Further, in act d) in order to generate the subtraction data sets, in each case, one of the mask data sets may be subtracted from the at least one second image data set of a corresponding slice and/or a corresponding volume.

A slice may describe an essentially flat volume area of the examination object. Further, the volume of the examination object may include a plurality of slices (e.g., running in parallel). In one embodiment, the at least one common slice and/or the at least one common volume of the examination object may be predetermined based on anatomical and/or geometric features and/or a marker object that may be mapped in the first image data sets and/or the at least one second image data set.

Further, the first image data sets and/or the at least one second image data set may map the common slice of the examination object using an arrangement (e.g., a two-dimensional arrangement) of image points (e.g., pixels). If the first image data sets and/or the at least one second image data set are time-resolved, the pixels may also have time intensity curves.

If the first image data sets and/or the at least one second image data set map a common volume of the examination object (e.g., including a plurality of slices), the first image data sets and/or the at least one second image data set may map the common volume using an arrangement (e.g., three-dimensional arrangement) of pixels (e.g., voxels).

The determination of the mask data sets in act c) may include averaging in layers and/or in lines and/or in columns and/or in pixels of the at least one combination of first image data sets. The averaging of the at least one combination of first image data sets in layers and/or in lines and/or in columns may describe averaging of the pixels of the first image data sets to be averaged. The pixels are arranged in a common spatial slice and/or line and/or column. Alternatively or additionally, the averaging of the at least one combination of the first image data sets in relation to one in the respective slice and/or line and/or column and/or in the respective pixel may take place in slices and/or in lines and/or in columns and/or in pixels (e.g., after applying a registration and/or movement correction to the first image data sets). This may, for example, result in a reassignment and/or spatial transformation of the first image data sets that each map a common slice and/or a common volume. The registration may, for example, be based on the anatomical and/or geometric features and/or the marker object, which may be mapped in the first image data sets and/or the at least one second image data set, and/or metadata.

For example, in act c), combinations of first image data sets may be averaged, each of which map a common slice and/or a common volume of the examination area. In one embodiment, the mask data sets may each have an image of a slice and/or a volume of the examination object.

In act d), one of the mask data sets of a corresponding slice and/or a corresponding volume may be subtracted from the at least one second image data set in order to generate the subtraction data sets. For example, in act d), the mask data sets (e.g., all the mask data sets) may be subtracted from the at least one second image data set that has an image of a corresponding slice and/or a corresponding volume.

As a result, a consistent combination of the first image data sets for determining the mask data sets and/or a consistent determination of the subtraction data sets with regard to the slice and/or the volume of the examination object mapped therein may be provided.

In a further embodiment of the method, the medical imaging device may be configured as a medical X-ray device. Further, the first image data sets may each have a plurality of first projection images of a plurality of first rotation runs of the medical X-ray device. In addition, the at least one second image data set may in each case have a plurality of second projection images of at least one second rotation run of the medical X-ray device. Further, act c) may further include a reconstruction of first slice images and/or first volume images of the examination object from the first projection images of a common first rotation run. Further, at least one of the mask data sets may include an averaging of at least one combination of the first slice images and/or the first volume images. Further, act d) includes a reconstruction of at least one second slice image and/or at least one second volume image of the examination object from the second projection images of a common second rotation run. In addition, in act d), in order to generate the subtraction data sets, one of the mask data sets may be subtracted from the at least one second slice image and/or the at least one second volume image.

The medical X-ray device may, for example, be configured as a medical C-arm X-ray device. In one embodiment, the medical X-ray device may have an X-ray source and a detector (e.g., an X-ray detector) that may be configured as a flat-panel detector and/or line detector. The X-ray source and the detector may be arranged in a defined arrangement (e.g., on a common C-arm) in a movable manner with respect to the examination object. To record the first projection images, the X-ray source may emit X-ray beams. The X-ray beams may be received and processed by the detector upon impinging on a surface of the detector, after interaction with the examination object. In this case, the X-ray beams may, for example, have the form of a cone beam and/or fan beam and/or parallel beam. In one embodiment, the first projection images may be recorded in a chronological sequence (e.g., one after the other). Further, the medical X-ray device (e.g., the defined arrangement of X-ray source and detector) may have been rotated around a spatial axis (e.g., around an isocenter) in order to record the plurality of first projection images of one of the first rotation runs in each case. A first rotation run may describe one rotation (e.g., complete rotation) of the defined arrangement (e.g., in a predetermined angular range). Alternatively or additionally, the defined arrangement of X-ray source and detector may have been moved along a predetermined trajectory (e.g., elliptical and/or circular and/or spiral) during one of the first rotation runs.

The plurality of second projection images may be recorded analogously to the plurality of first projection images using the medical X-ray device. The medical X-ray device (e.g., the defined arrangement of X-ray source and detector) may have been rotated around a further spatial axis (e.g., a further isocenter) to record the multiple second projection images of the at least one second rotation run. In one embodiment, the further spatial axis (e.g., the further isocenter) of the at least one second rotation run coincides with the spatial axis (e.g., the isocenter) of the first rotation runs. In addition, the defined arrangement of X-ray source and detector may have been moved along a predetermined further trajectory (e.g., elliptical and/or circular and/or spiral) during the at least one second rotation run. In this case, the further trajectory of the at least one second rotation run may coincide, at least in sections, with the trajectory of the first rotation runs.

In act c), the first slice images and/or the first volume images of the examination object may be reconstructed from the first projection images of a common first rotation run. In this case, the reconstruction of the first slice images and/or the first volume images may include applying a tomography algorithm to the plurality of first projection images in each case of a common first rotation run (e.g., an inverse radon transformation and/or a filtered back projection). The first slice images may each have an image of a spatial slice of the examination object within the first temporal phase. Further, the first volume images may have an image of a spatial volume of the examination object within the first temporal phase. For example, the first volume images may each include a plurality of first slice images.

The at least one second slice image and/or the at least one second volume image may (e.g., analogously to the first slice images and/or first volume images) be reconstructed from the second projection images of a common second rotation run. The reconstruction of the at least one second slice image and/or the at least one second volume image may include applying a tomography algorithm to the plurality of second projection images in each case of a common second rotation run (e.g., an inverse radon transformation and/or a filtered back projection). The at least one second slice image may have an image of a spatial slice of the examination object in each case within the second temporal phase. Further, the at least one second volume image may have an image of a spatial volume of the examination object within the second temporal phase. For example, the at least one second volume image may in each case include a plurality of second slice images.

The reconstruction of the first slice images and/or the first volume images may include applying a movement correction to the respective first projection images of a common first rotation run. Analogously thereto, the reconstruction of the at least one second slice image and/or the at least one second volume image may include applying a movement correction to the respective second projection images of a common second rotation run.

In one embodiment, at least one of the mask data sets may include an averaging (e.g., weighted averaging) of at least one combination of the first slice images and/or the first volume images. For this purpose (e.g., in each case), at least two of the first slice images and/or the first volume images may be averaged. The averaging of the at least one combination of the first slice images and/or the first volume images may be carried out in slices and/or in rows and/or in columns and/or in pixels. Further, the mask data sets may include at least one of the first slice images and/or at least one of the first volume images.

Further, act c) may include a registration (e.g., a movement correction) of the first slice images to be combined and/or the first volume images to be combined.

In order to generate the subtraction data sets in act d), one of the mask data sets may in each case be subtracted from the at least one second slice image and/or the at least one second volume image. The subtraction may take place (e.g., analogously to the averaging) in slices and/or in rows and/or in columns and/or in pixels. For example, to generate the subtraction data sets, each of the mask data sets may be subtracted from at least one second slice image and/or volume image. If a plurality of second image data sets are received in act b), each of the mask data sets may be subtracted from each of the second slice images and/or the second volume images in order to generate the subtraction data sets.

Further, act d) may include registration (e.g., a movement correction) of the mask data sets to be subtracted with the at least one second slice image and/or the at least one second volume image.

In one embodiment, the embodiment may enable three-dimensional, spatially resolved mapping of the change in the examination area in the subtraction data sets.

In a further embodiment of the method, at least one of the mask data sets may include an averaging of at least one combination of the first projection images. The first projection images have a common first projection direction. Further, in act d), in order to generate the subtraction data sets, in each case, one of the mask data sets may be subtracted from the at least one second projection image with a corresponding projection direction.

By averaging the at least one combination of the first projection images, it may be provided that the first projection images to be averaged have a common imaging geometry for imaging the examination object. The first projection images have a common (e.g., corresponding) first projection direction. For example, the mask data sets may each have an image of the examination object along one of the first projection directions. In addition, the mask data sets may include at least one of the first projection images.

In act d), in order to generate the subtraction data sets, in each case, one of the mask data sets with corresponding first and second projection directions may be subtracted from the at least one second projection image. For example, in act d), the mask data sets (e.g., all the mask data sets) may be subtracted from the at least one second projection image that has a first projection direction corresponding to the second projection direction of the at least one second projection image.

As a result, it may be provided that the mask data sets to be subtracted from the at least one second projection image each have a corresponding imaging geometry for imaging the examination object.

In a further embodiment of the method, the at least one second image data set may map a contrast medium arranged in the second temporal phase in the examination object as the change.

The contrast medium may be, for example, an X-ray contrast medium (e.g., an X-ray opaque contrast medium) and/or an ultrasound contrast medium and/or a magnetic resonance contrast medium. In one embodiment, the contrast medium may have been applied to the examination object before the start of the method of one or more of the present embodiments. In one embodiment, the contrast medium arranged at least partially in the examination area (e.g., a propagation movement of the contrast medium and/or a contrast medium bolus) may be mapped in the at least one second image data set. In one embodiment, the contrast medium may be arranged (e.g., selectively) during the second temporal phase in the hollow organ of the examination object to be mapped. As a result, a contrasted image of the hollow organ may be made possible in the at least one second image data set and consequently in the subtraction data sets.

In a further embodiment of the method, the image quality parameters in act e) may be determined by applying an image quality metric to one of the subtraction data sets in each case. Further, the image quality metric may evaluate an artifact level and/or signal-to-noise-ratio in the respective subtraction data set.

The image quality metric may be configured to evaluate an occurrence and/or an expression of image artifacts (e.g., motion artifacts and/or metal artifacts and/or reconstruction artifacts) in the subtraction data sets. In one embodiment, the image quality metric may provide one image quality parameter (e.g., normalized) for each of the subtraction data sets, which evaluates the artifact level and/or signal-to-noise-ratio in the respective subtraction data set. Further, the image quality metric may be based on an entropy and/or total variation in the subtraction data sets. In addition, the image quality metric may be a consistency condition with regard to the image features that may be contained in the first image data sets and/or in the at least one second image data set and/or the respective subtraction data set.

This enables a uniform and/or standardized evaluation of the image quality of the subtraction data sets. Further, this makes it possible to determine (e.g., to select) the optimum subtraction data set by comparing the image quality parameters of the plurality of subtraction data sets.

In a further embodiment of the method, the image quality metric may be based on artificial intelligence.

The image quality metric may be trained using a method of machine learning. For example, the image quality metric may include a trained function that is trained by a method of machine learning. The image quality metric (e.g., the trained function) may, for example, be a neural network (e.g., a convolutional neural network (CNN) or a network including a convolutional layer.

The trained function maps input data to output data. In this case, the output data may, for example, continue to depend on one or more parameters of the trained function. The one or more parameters of the trained function may be determined and/or adapted by training. The determination and/or adaptation of the one or more parameters of the trained function may be based, for example, on a pair of training input data items and associated comparison output data. The trained function is applied to the training input data to generate training mapping data. For example, the determination and/or the adaptation may be based on a comparison of the training mapping data and the comparison output data. In general, a trainable function (e.g., a function with one or more parameters that have not yet been adapted) is also referred to as a trained function.

Other terms for trained functions are trained mapping specification, mapping specification with trained parameters, function with trained parameters, algorithm based on artificial intelligence, and machine learning algorithm. An example of a trained function is an artificial neural network, the edge weights of the artificial neural network corresponding to the parameters of the trained function. Instead of the term "neural network", the term "neural net" may also be used. For example, a trained function may also be a deep neural network or deep artificial neural network. Another example of a trained function is a "support vector machine", and, for example, other machine learning algorithms may also be used as a trained function.

The trained function may be trained, for example, by back propagation. First, training mapping data may be determined by applying the trained function to training input data. Thereafter, a deviation between the training mapping data and the comparison output data may be determined by applying an error function to the training mapping data and the comparison output data. Further, at least one parameter (e.g., a weighting) of the trained function (e.g., of the neural network) may be iteratively adapted based on a gradient of the error function with respect to the at least one parameter of the trained function. As a result, the deviation between the training mapping data and the comparison output data may be minimized during the training of the trained function.

In one embodiment, the trained function (e.g., the neural network) has an input layer and an output layer. In this case, the input layer may be configured to receive input data. Further, the output layer may be configured to provide imaging data. In this case, the input layer and/or the output layer may each include a plurality of channels (e.g., neurons).

The image quality metric (e.g., the trained function) may be configured to process a subtraction data set as input data and to provide the image quality parameter as output data.

For training of the image quality metric (e.g., the trained function), training input data including training subtraction data sets may be determined by applying acts a) to d) to first and second training image data sets. In this case, the first and second training image data sets may, for example, have all the features and properties of the first image data sets and of the at least one second image data set. For example, the first and/or second training image data sets may be simulated. Further, simulating at least some of the first and/or second image data sets may include applying a transformation (e.g., rigid and/or non-rigid) to one of the first and/or second image data sets. As a result, for example, motion artifacts that may be caused by a movement of the examination object may be simulated for training the trained function.

Further, the comparison output data may be determined by applying at least one further image quality metric to the training input data. The at least one further image quality metric may be based, for example, on an entropy and/or total variation of the training input data. Alternatively or additionally, the comparison output data may be determined by annotating the training input data (e.g., by an input by a user; the input evaluates the image quality of the training input data). Further, the training may be carried out, for example, by monitored training.

As a result, a particularly robust and precise determination of the image quality parameters in act e) may be made possible.

In a further embodiment of the method, the medical imaging device and/or the further medical imaging device may be configured as a medical X-ray device and/or a computed tomography system and/or a magnetic resonance system and/or a positron emission tomography system and/or an ultrasonic device.

As a result, an imaging modality (e.g., adapted to the change in the examination object to be imaged) may be used to record and/or provide the first image data sets and/or the at least one second image data set.

In a second aspect, the present embodiments relate to a medical imaging device that is configured to carry out a method of one or more of the present embodiments for providing an optimum subtraction data set.

The medical imaging device may, for example, be configured as a medical X-ray device (e.g., a medical C-arm X-ray device) and/or a computed tomography system (CT) and/or a magnetic resonance system (MRT) and/or a positron emission tomography system (PET) and/or an ultrasonic device. In one embodiment, the medical imaging device may have a provision unit that is configured to carry out the acts of the method of one or more of the present embodiments.

The advantages of the medical imaging device of one or more of the present embodiments essentially correspond to the advantages of the method of one or more of the present embodiments for providing an optimum subtraction data set. Features, advantages, or alternative embodiments mentioned here may also be transferred to the other subject matter and vice versa.

In a third aspect, the present embodiments relate to a computer program product having a computer program that may be loaded directly into a memory of a provision unit, having program sections to carry out all the acts of the method of one or more of the present embodiments for providing an optimum subtraction data set when the program sections are executed by the provision unit. In this case, the computer program product may include software with source code that has yet to be compiled and linked or that only is to be interpreted, or an executable software code that only is to be loaded into the provision unit for execution. Using the computer program product, the method for providing an optimum subtraction data set may be carried out quickly, identically repeatably, and robustly using a provision unit. The computer program product is configured such that the computer program product may execute the method acts according to the present embodiments using the provision unit.

The computer program product is stored, for example, on a computer-readable storage medium or on a network or server, from where the computer program product may be loaded into the processor of a provision unit that may be directly connected to the provision unit or may be configured as part of the provision unit. Further, control information of the computer program product may be stored on an electronically readable data carrier. The control information of the electronically readable data carrier may be configured such that the control information carries out a method according to the present embodiments when the data carrier is used in a provision unit. Examples of electronically readable data carriers are a DVD, a magnetic tape, or a USB stick on which electronically readable control information (e.g., software) is stored. When this control information is read from the data carrier and stored in a provision unit, all the embodiments according to the present embodiments of the methods described previously may be carried out.

The present embodiments may further originate from a computer-readable storage medium and/or electronically readable data carrier on which program sections readable and executable from a provision unit are stored in order to carry out all the acts of the method for providing an optimum subtraction data set when the program sections are executed by the provision unit.

A largely software-based implementation has the advantage that even previously used provision units may be retrofitted in a simple manner by a software update in order to work in the manner according to the present embodiments. In addition to the computer program, such a computer program product may optionally include additional components such as, for example, documentation and/or additional components, as well as hardware components such as, for example, hardware keys (e.g., dongles, etc.) for using the software.

BRIEF DESCRIPTION OF THE DRAWINGS

The same reference characters are used for the same features in different figures.

DETAILED DESCRIPTION

Figure 1:
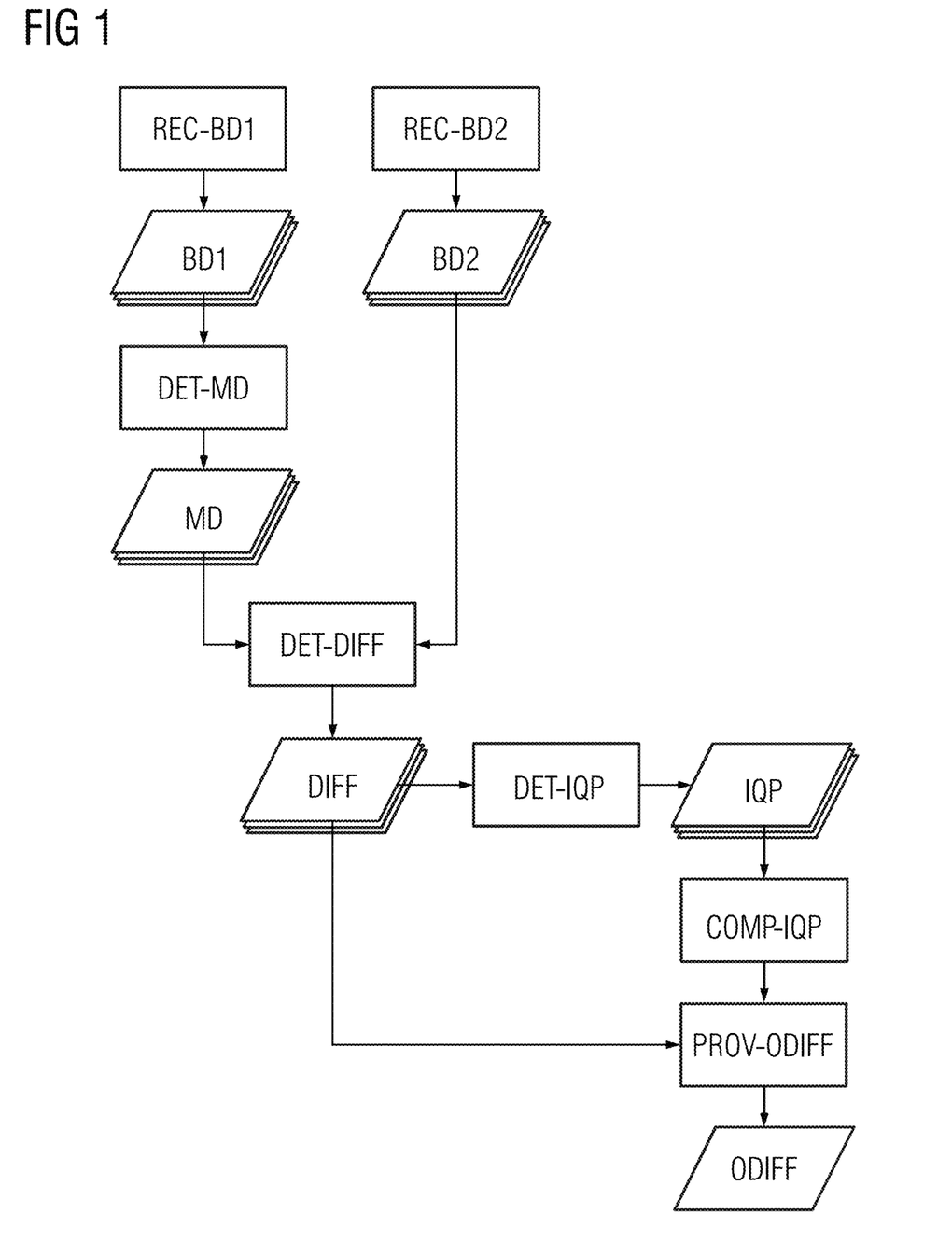
FIGS. 1 to 3 are diagrammatic views of various embodiments of a method for providing an optimum subtraction data set.

FIG. 1 shows a diagrammatic view of an embodiment of a method for provision of an optimum subtraction data set. In a first act a), first image data sets BD1 may be received REC-BD1. In this case, the first image data sets BD1 may map an examination object within a first temporal phase. In addition, the first image data sets BD1 may be recorded by a medical imaging device. In a second act b), at least one second image data set BD2 may be received REC-BD2. In this case, the at least one second image data set BD2 may map the examination object within a second temporal phase. In addition, the at least one second image data set BD2 may be recorded by the medical imaging device or another medical imaging device.

The medical imaging device and/or the other medical imaging device may be configured, for example, as a medical X-ray device (e.g., a medical C-arm X-ray device, and/or a computed tomography system, and/or a magnetic resonance system, and/or a positron emission tomography system, and/or an ultrasonic device).

Further, the at least one second image data set BD2 may map a change in the examination object compared to the first temporal phase. For example, the at least one second image data set BD2 may map a contrast medium arranged in the examination object in the second temporal phase as the change. In a third act c), mask data sets MD may be determined DET-MD. The mask data sets MD may include at least one of the first image data sets BD1 and/or an averaging of at least one combination of the first image data sets BD1. In a fourth act d), subtraction data sets DIFF may be determined in each case by subtracting one of the mask data sets MD from the at least one second image data set BD2, DET-DIFF. In a fifth act e), an image quality parameter IQP may be determined for each of the subtraction data sets DIFF DET-IQP. The determination DET-IQP of the image quality parameters IQP may take place by applying an image quality metric to one of the subtraction data sets DIFF in each case. The image quality metric may evaluate an artifact level and/or signal-to-noise-ratio in the respective subtraction data set DIFF. In addition, the image quality metric may be based on artificial intelligence.

Further, in a sixth act f), the optimum subtraction data set ODIFF may be provided by a comparison COMP-IQP of the image quality parameters IQP, PROV-ODIFF.

For example, the mask data sets MD may include averaging of all possible combinations of first image data sets BD1. For a number z of first image data sets BD1, there may be $$2^z - 1$$

possible combinations, including the individual first image data sets BD1.

Further, the first image data sets BD1 and the at least one second image data set BD2 may each map at least one common slice and/or an at least partially common volume of the examination object. To determine DET-MD of the mask data sets MD, the at least one combination of the first image data sets BD1 may be averaged in slices and/or in rows and/or in columns and/or in pixels. Further, in act d), in order to generate DET-DIFF of the subtraction data sets DIFF, one of the mask data sets MD may be subtracted from the at least one second image data set BD2 of a corresponding slice and/or a corresponding volume.

Figure 2:
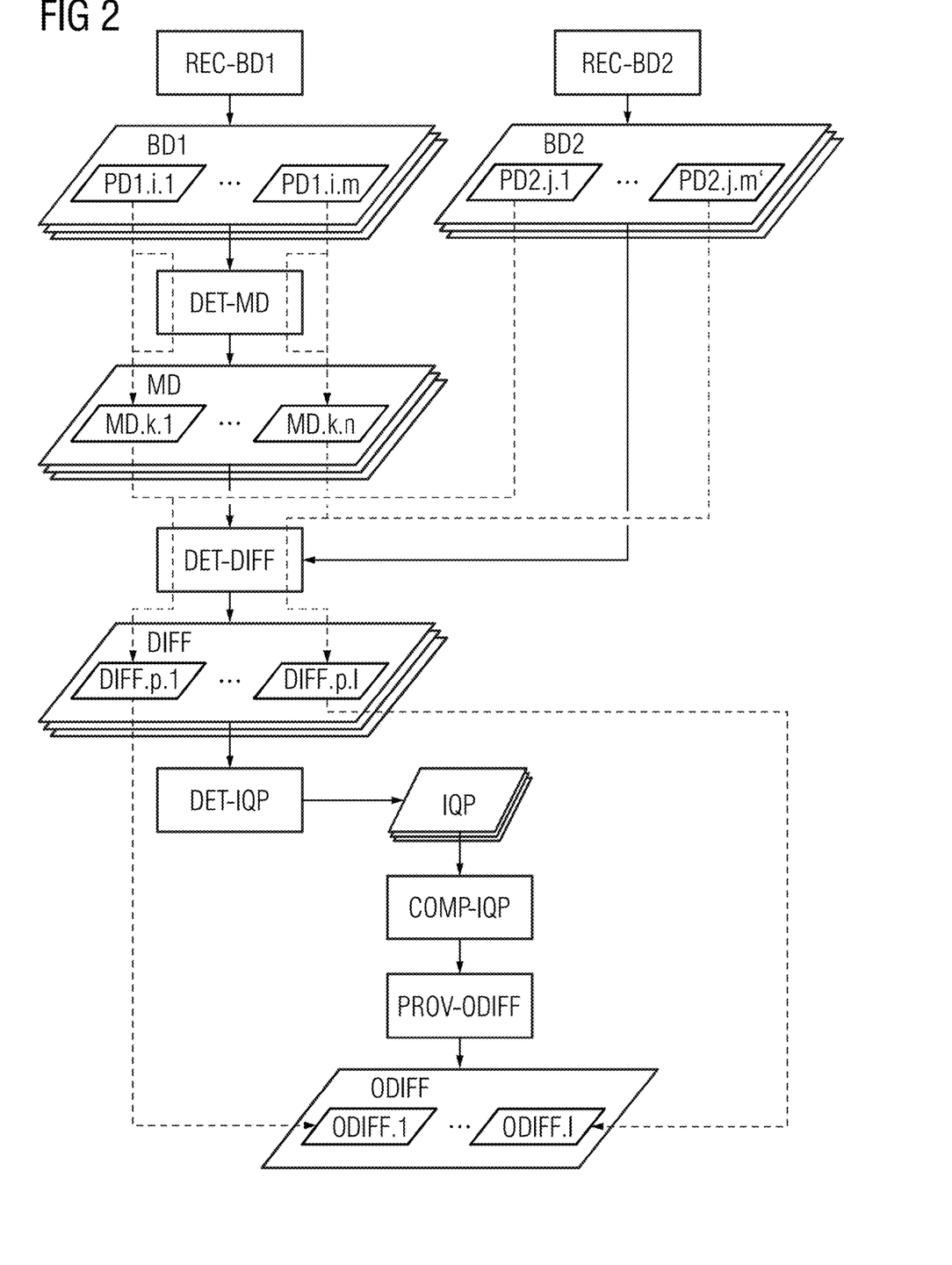

FIG. 2 shows a diagrammatic view of a further embodiment of the method for provision of PROV-ODIFF of an optimum subtraction data set ODIFF. In this case, the first image data sets BD1 may have a plurality of first projection images PD1.$i$.1 to PD1.$i$.m of the examination object along at least one first projection direction. Further, the at least one second image data set BD2 may have at least one second projection image (e.g., a plurality of second projection images PD2.$j$.1 to PD2.$j$.m') of the examination object along at least one second projection direction. In this case, at least one of the first projection directions and at least one of the second projection directions may coincide.

In addition, at least one of the mask data sets MD.k.1 to MD.k.n may include an averaging of at least one combination of the first projection images PD1.$i$.1 to PD1.$i$.m. First projection images to be combined each have a common first projection direction. In addition, in act d), in order to generate DET-DIFF of the subtraction data sets DIFF.p.1 to DIFF.p.1, one of the mask data sets MD.k.1 to MD.k.n may be subtracted from the at least one second projection image PD2.$j$.1 to PD2.$j$.m' with a corresponding projection direction.

Figure 3:
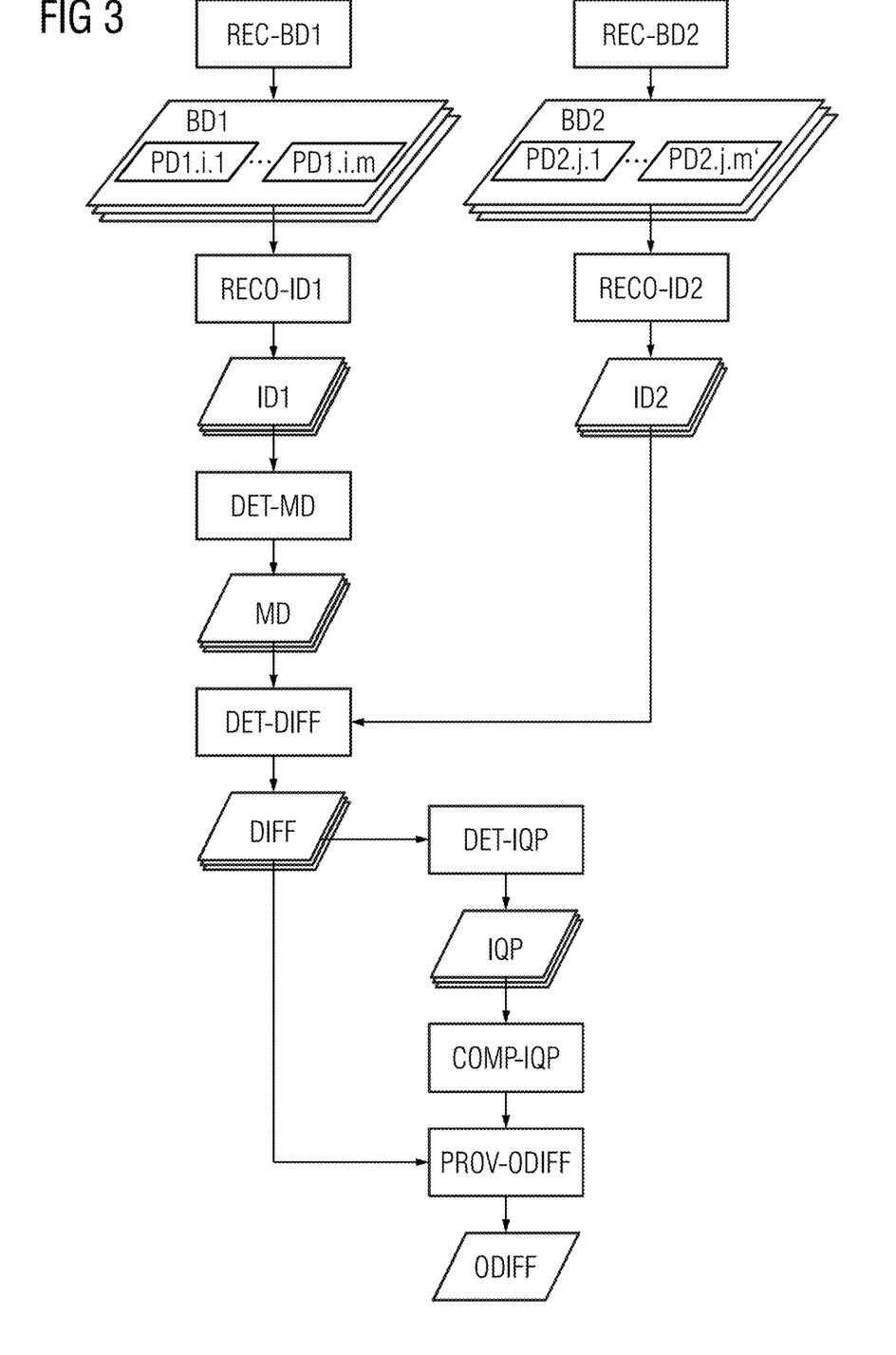

FIGS. 2 and 3 show the first projection images PD1.$i$.1 to PD1.$i$.m of a, for example, i-th of the plurality of first image data sets BD1 representative of the first projection images of the plurality of first image data sets BD1. The first projection images PD1.$i$.1 to PD1.$i$.m may be recorded, for example, along a number of m projection directions. If a plurality of second image data sets are received in act b), the second projection images PD2.$j$.1 to PD2.$j$.m' of a, for example, j-th of the plurality of second image data sets BD2 are shown as representative of the second projection images of the plurality of second image data sets BD2. The second projection images PD2.$j$.1 to PD2.$j$.m' may be recorded, for example, along a number of m' projection directions. In addition, a, for example, k-th mask data set MD.k.1 to MD.k.n is shown diagrammatically as representative of the plurality of mask data sets. Further, the subtraction data sets DIFF.p.1 to DIFF.p.1 are shown diagrammatically for a, for example, p-th subtraction of a, for example, k-th mask data set MD.k.1 to MD.k.n from the at least one second projection image PD2.$j$.1 to PD2.$j$.m' with a corresponding projection direction.

FIG. 3 shows a diagrammatic view of a further embodiment of the method for provision PROV-ODIFF of an optimum subtraction data set ODIFF. The medical imaging device may be configured as a medical X-ray device. In addition, the first image data sets BD1 may each have a plurality of first projection images PD1.$i$.1 to PD1.$i$.m of a plurality of first rotation runs of the medical X-ray device. In addition, the at least one second image data set BD2 may in each case have a plurality of second projection images PD2.$j$.1 to PD2.$j$.m' of at least one second rotation run (e.g., a plurality of second rotation runs) of the medical X-ray device. In act c), a reconstruction RECO-ID1 of first slice images and/or first volume images ID1 of the examination object from the first projection images PD1.$i$.1 to PD1.$i$.m may also each include a common first rotation run. At least one of the mask data sets MD may include an averaging of at least one combination of the first slice images and/or the first volume images ID1. Further, act d) may include a reconstruction RECO-ID2 of at least one second slice image and/or at least one second volume image ID2 of the examination object from the second projection images PD2.$j$.1 to PD2.$j$.m' in each case of a common second rotation run. Further, in act d), in order to generate DET-DIFF of the subtraction data sets DIFF, in each case, one of the mask data sets MD may be subtracted from the at least one second slice image and/or the at least one second volume image ID2.

Figure 4:
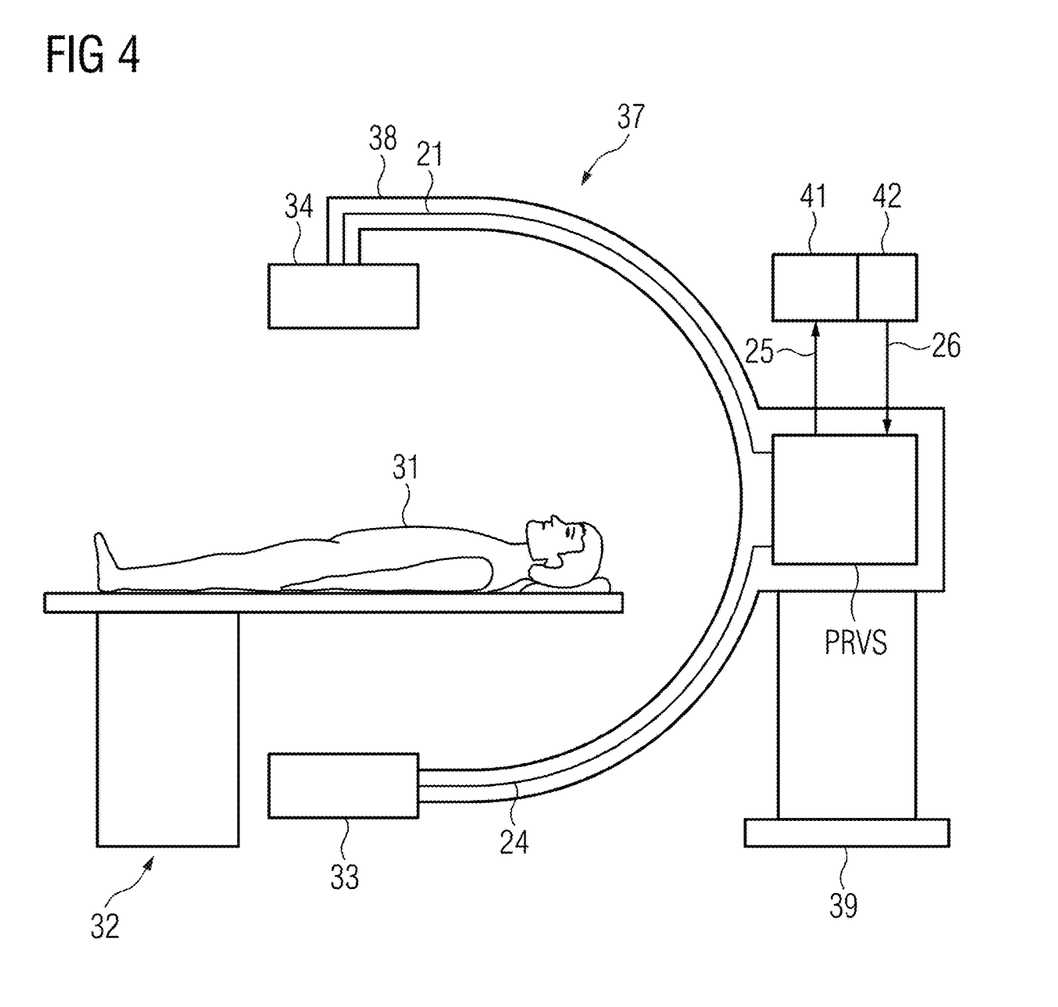
FIG. 4 is a diagrammatic view of one embodiment of a medical C-arm X-ray device.

FIG. 4 shows a diagrammatic view of a medical C-arm X-ray device 37 by way of example for a medical imaging device of one or more of the present embodiments. In this case, the medical C-arm X-ray device 37 may include a provision unit PRVS. Further, the medical C-arm X-ray device 37 (e.g., the provision unit PRVS) may be configured to carry out a method of one or more of the present embodiments for the provision PROV-ODIFF of an optimum subtraction data set ODIFF.

In this case, the medical C-arm X-ray device 37 may include a detector 34 (e.g., an X-ray detector) and an X-ray source 33. For recording the first image data sets BD1 (e.g., the first projection images PD1.$i$.1 to PD1.$i$.m) and/or the at least one second image data set BD2 (e.g., the second projection images PD2.$j$.1 to PD2.$j$.m'), an arm 38 of the C-arm X-ray device 37 may be mounted movably about one or more axes. Further, the medical C-arm X-ray device 37 may include a movement apparatus 39 that enables the C-arm X-ray device 37 to move in space (e.g., a wheel system and/or a rail system and/or a robotic arm).

To record the first image data sets BD1 and/or the at least one second image data set BD2 from an examination object 31 arranged on a patient support facility 32, the provision unit PRVS may send a signal 24 to the X-ray source 33. The X-ray source 33 may then emit an X-ray beam. When the X-ray beam impinges on a surface of the detector 34 after an interaction with the examination area, the detector 34 may send a signal 21 to the provision unit PRVS. The provision unit PRVS may, for example, use the signal 21 to receive the first image data sets BD1 and/or the at least one second image data set BD2, REC-BD1, REC-BD2.

Further, the medical C-arm X-ray device 37 may include an input unit 42 (e.g., a keyboard, and/or a display unit 41, such as a monitor, and/or display). The input unit 42 may be integrated into the display unit 41, for example, in the case of a capacitive and/or resistive input display. A control of the medical C-arm X-ray device 37 (e.g., of the method for the provision PROV-ODIFF of an optimum subtraction data set ODIFF) may be made possible by an input by the user on the input unit 42. For this purpose, the input unit 42 may, for example, send a signal 26 to the provision unit PRVS.

Further, the display unit 41 may be configured to display information and/or graphical representations of information from the medical C-arm X-ray device 37 and/or the provision unit PRVS and/or further components. For this purpose, the provision unit PRVS may, for example, send a signal 25 to the display unit 41. For example, the display unit 41 may be configured to display a graphical representation of the first image data sets BD1 and/or the at least one second image data set BD2 and/or the mask data sets MD and/or the subtraction data sets DIFF and/or the optimum subtraction data set ODIFF.

The diagrammatic views in the figures described do not depict any scale or size ratio.

The methods described in detail above and the apparatus shown are merely exemplary embodiments that may be modified in a wide variety of ways by a person skilled in the art without departing from the scope of the invention. Further, the use of the indefinite articles "a" or "an" does not exclude the possibility of the relevant features appearing multiple times. Likewise, the terms "unit" and "element" do not exclude the possibility of the relevant components consisting of a plurality of interacting subcomponents that may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing an optimum subtraction data set, the method comprising:
   receiving first image data sets, wherein the first image data sets map an examination object within a first temporal phase, wherein the first image data sets are recorded by a medical imaging device;
   receiving at least one second image data set, wherein the at least one second image data set maps the examination object within a second temporal phase, wherein the at least one second image data set is recorded by the medical imaging device or another medical imaging device, wherein the at least one second image data set maps a change in the examination object compared to the first temporal phase;
   determining mask data sets, wherein the mask data sets comprise at least one of the first image data sets, an averaging of at least one combination of the first image data sets, or a combination thereof;
   generating subtraction data sets, the generating of the subtraction data sets comprising subtracting each of the mask data sets from the at least one second image data set;
   determining a respective image quality parameter for the subtraction data sets;
   providing an optimum subtraction data set using a comparison of the image quality parameters; and
   storing, by a memory, the optimum subtraction data set, displaying, by a display, the optimum subtraction data set, or a combination thereof.

2. The method of claim 1, wherein the mask data sets comprise averaging of all possible combinations of the first image data sets.

3. The method of claim 1, wherein the first image data sets include a plurality of first projection images of the examination object along at least one first projection direction,
   wherein the at least one second image data set includes at least one second projection image of the examination object along at least one second projection direction, and
   wherein one or more first projection directions of the at least one first projection direction and one or more second projection directions of the at least one second projection direction correspond.

4. The method of claim 1, wherein the first image data sets and the at least one second image data set each map at least one common layer, an at least partially common volume, or at least one common layer and at least partially common volume of the examination object,
   wherein at least one of the mask data sets comprises an averaging of at least one combination of the first image data sets,
   wherein determining the mask data sets comprises averaging the at least one combination of the first image data sets in layers, in lines, in columns, in pixels, or any combination thereof, and
   wherein generating the subtraction data sets comprises subtracting, in each case, one of the mask data sets from the at least one second image data set of a corresponding layer, a corresponding volume, or a corresponding layer and a corresponding volume.

5. The method of claim 3, wherein the medical imaging device is configured as a medical X-ray device,
   wherein each of the first image data sets has a plurality of first projection images of a plurality of first rotation runs of the medical X-ray device,
   wherein each second image data set of the at least one second image data set includes a plurality of second projection images of at least one second rotation run of the medical X-ray device,
   wherein determining the mask data sets further comprises reconstructing first slice images, first volume images, or the first slice images and the first volume images of the examination object from the first projection images in each case of a common first rotation run,
   wherein at least one of the mask data sets comprises an averaging of at least one combination of the first slice images, the first volume images, or the first slice images and the first volume images,
wherein generating the subtraction data sets comprises reconstructing at least one second slice image, at least one second volume image, or the at least one second slice image and the at least one second volume image of the examination object from the second projection images in each case of a common second rotation run,
wherein generating the subtraction data sets comprises subtracting, in each case, one of the mask data sets from the at least one second slice image, the at least one second volume image, or the at least one second slice image and the at least one second volume image.

6. The method of claim 3, wherein at least one of the mask data sets comprises an averaging of at least one combination of the first projection images that have a common first projection direction,
wherein generating the subtraction data sets comprises subtracting, in each case, one of the mask data sets from the at least one second projection image with a corresponding projection direction.

7. The method of claim 1, wherein the at least one second image data set maps a contrast medium arranged in the examination object in the second temporal phase as the change.

8. The method of claim 1, wherein determining the image quality parameters comprises applying an image quality metric to a respective one of the subtraction data sets, and
wherein the image quality metric evaluates an artifact level, a signal-to-noise ratio, or the artifact level and the signal-to-noise ratio in the respective subtraction data set.

9. The method of claim 8, wherein the image quality metric is based on artificial intelligence.

10. The method of claim 1, wherein the medical imaging device, the other medical imaging device, or the medical imaging device and the other medical imaging device are configured as a medical X-ray device, a computed tomography system, a magnetic resonance system, a positron emission tomography system, an ultrasonic device, or any combination thereof.

11. A medical imaging device comprising:
a processor configured to provide an optimum subtraction data set, the provision of the optimum subtraction data set comprising:
receipt of first image data sets, wherein the first image data sets map an examination object within a first temporal phase, wherein the first image data sets are recorded by a medical imaging device;
receipt of at least one second image data set, wherein the at least one second image data set maps the examination object within a second temporal phase, wherein the at least one second image data set is recorded by the medical imaging device or another medical imaging device, wherein the at least one second image data set maps a change in the examination object compared to the first temporal phase;
determination of mask data sets, wherein the mask data sets comprise at least one of the first image data sets, an averaging of at least one combination of the first image data sets, or a combination thereof;
generation of subtraction data sets, the generation of the subtraction data sets comprising subtraction of each of the mask data sets from the at least one second image data set;
determination of a respective image quality parameter for the subtraction data sets;
provision of an optimum subtraction data set using a comparison of the image quality parameters; and
store, by a memory, the optimum subtraction data set, display, by a display, the optimum subtraction data set, or a combination thereof.

12. A non-transitory computer-readable storage medium that stores instructions executable by one or more processors to provide an optimum subtraction data set, the instructions comprising:
receiving first image data sets, wherein the first image data sets map an examination object within a first temporal phase, wherein the first image data sets are recorded by a medical imaging device;
receiving at least one second image data set, wherein the at least one second image data set maps the examination object within a second temporal phase, wherein the at least one second image data set is recorded by the medical imaging device or another medical imaging device, wherein the at least one second image data set maps a change in the examination object compared to the first temporal phase;
determining mask data sets, wherein the mask data sets comprise at least one of the first image data sets, an averaging of at least one combination of the first image data sets, or a combination thereof;
generating subtraction data sets, the generating of the subtraction data sets comprising subtracting each of the mask data sets from the at least one second image data set;
determining a respective image quality parameter for the subtraction data sets;
providing an optimum subtraction data set using a comparison of the image quality parameters; and
storing, by a memory, the optimum subtraction data set, displaying, by a display, the optimum subtraction data set, or a combination thereof.

13. The non-transitory computer-readable storage medium of claim 12, wherein the mask data sets comprise averaging of all possible combinations of the first image data sets.

14. The non-transitory computer-readable storage medium of claim 12, wherein the first image data sets include a plurality of first projection images of the examination object along at least one first projection direction,
wherein the at least one second image data set includes at least one second projection image of the examination object along at least one second projection direction, and
wherein one or more first projection directions of the at least one first projection direction and one or more second projection directions of the at least one second projection direction correspond.

15. The non-transitory computer-readable storage medium of claim 12, wherein the first image data sets and the at least one second image data set each map at least one common layer, an at least partially common volume, or at least one common layer and at least partially common volume of the examination object,
wherein at least one of the mask data sets comprises an averaging of at least one combination of the first image data sets,
wherein determining the mask data sets comprises averaging the at least one combination of the first image data sets in layers, in lines, in columns, in pixels, or any combination thereof, and
wherein generating the subtraction data sets comprises subtracting, in each case, one of the mask data sets from the at least one second image data set of a corresponding layer, a corresponding volume, or a corresponding layer and a corresponding volume.

16. The non-transitory computer-readable storage medium of claim 14, wherein the medical imaging device is configured as a medical X-ray device,
wherein each of the first image data sets has a plurality of first projection images of a plurality of first rotation runs of the medical X-ray device,
wherein each second image data set of the at least one second image data set includes a plurality of second projection images of at least one second rotation run of the medical X-ray device,
wherein determining the mask data sets further comprises reconstructing first slice images, first volume images, or the first slice images and the first volume images of the examination object from the first projection images in each case of a common first rotation run,
wherein at least one of the mask data sets comprises an averaging of at least one combination of the first slice images, the first volume images, or the first slice images and the first volume images,
wherein generating the subtraction data sets comprises reconstructing at least one second slice image, at least one second volume image, or the at least one second slice image and the at least one second volume image of the examination object from the second projection images in each case of a common second rotation run,
wherein generating the subtraction data sets comprises subtracting, in each case, one of the mask data sets from the at least one second slice image, the at least one second volume image, or the at least one second slice image and the at least one second volume image.

17. The non-transitory computer-readable storage medium of claim 14, wherein at least one of the mask data sets comprises an averaging of at least one combination of the first projection images that have a common first projection direction,
wherein generating the subtraction data sets comprises subtracting, in each case, one of the mask data sets from the at least one second projection image with a corresponding projection direction.

18. The non-transitory computer-readable storage medium of claim 12, wherein the at least one second image data set maps a contrast medium arranged in the examination object in the second temporal phase as the change.

* * * * *